(12) United States Patent
Alotaibi et al.

(10) Patent No.: US 9,788,919 B1
(45) Date of Patent: Oct. 17, 2017

(54) CENTRIC RELATION BITE REGISTRATION TOOL

(71) Applicant: KING SAUD UNIVERSITY, Riyadh (SA)

(72) Inventors: Hanan Nejer Sahil Alotaibi, Riyadh (SA); Sara Mohammad Al Taweel, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 53 days.

(21) Appl. No.: 15/169,706

(22) Filed: May 31, 2016

(51) Int. Cl.
*A61C 8/00* (2006.01)
*A61C 19/05* (2006.01)

(52) U.S. Cl.
CPC ............ *A61C 8/0001* (2013.01); *A61C 19/05* (2013.01)

(58) Field of Classification Search
CPC .............................. A61C 8/0001; A61C 19/05
See application file for complete search history.

(56) References Cited

U.S. PATENT DOCUMENTS

| | | | | |
|---|---|---|---|---|
| 1,338,415 A * | 4/1920 | Barrow | .................. | A61C 19/05 433/72 |
| 2,301,358 A * | 11/1942 | Ballard | .................. | A61C 19/05 433/69 |
| 2,552,829 A * | 5/1951 | Wilkinson | ............. | A61C 19/05 433/68 |
| 2,562,106 A * | 7/1951 | Leathers | ................ | A61C 19/05 433/69 |
| 2,644,233 A * | 7/1953 | Shmukler | ............... | A61C 11/02 433/60 |
| 2,738,583 A * | 3/1956 | Green | .................... | A61C 19/05 433/69 |
| 2,792,629 A * | 5/1957 | Green | .................... | A61C 19/05 433/69 |
| 3,068,570 A * | 12/1962 | Thompson | ............. | A61C 19/05 433/69 |
| 3,153,282 A * | 10/1964 | Brewer | .................. | A61C 19/05 433/214 |
| 3,381,377 A * | 5/1968 | Grayson | ................ | A61C 19/05 433/27 |
| 5,188,529 A * | 2/1993 | Luth | ...................... | A61C 19/05 433/68 |

(Continued)

FOREIGN PATENT DOCUMENTS

RU    2 321 375 C1    4/2008

*Primary Examiner* — Cris L Rodriguez
*Assistant Examiner* — Hao D Mai
(74) *Attorney, Agent, or Firm* — Richard C. Litman

(57) ABSTRACT

The centric relation bite registration tool is a tool for recording the centric relation of a patient's mandible in order to obtain proper occlusion to fabricate a full mouth fixed dental prosthesis. The centric relation bite registration tool includes both a vertically adjustable portion and a horizontally adjustable portion. The vertically adjustable portion is adapted for mounting in a dental implant in the patient's mandibular arch, and the horizontally adjustable portion is adapted for mounting in a dental implant in the patient's maxillary arch. The vertically adjustable portion and the horizontally adjustable portion are releasably secured to one another between the mandibular and maxillary arches providing a single tool which is both horizontally and vertically adjustable for recordation of the proper occlusion between the patient's mandible and maxilla.

5 Claims, 5 Drawing Sheets

(56) References Cited

U.S. PATENT DOCUMENTS

| | | | | |
|---|---|---|---|---|
| 5,597,303 | A | 1/1997 | Simmons | |
| 6,106,285 | A * | 8/2000 | Kwak | A61C 19/05 433/68 |
| 6,109,917 | A * | 8/2000 | Lee | A61C 19/045 433/68 |
| 6,979,195 | B2 * | 12/2005 | Skarky | A61C 19/05 433/34 |
| 8,556,626 | B2 * | 10/2013 | Evenson | A61C 19/052 433/54 |
| 2005/0112523 | A1 * | 5/2005 | Massad | A61C 11/06 433/68 |
| 2006/0172254 | A1 * | 8/2006 | Shindo | A61C 7/36 433/68 |
| 2012/0052463 | A1 * | 3/2012 | Pollet | A61C 8/0001 433/172 |
| 2013/0157217 | A1 * | 6/2013 | LeBeau | A61C 8/0001 433/68 |
| 2013/0203009 | A1 * | 8/2013 | Mutsafi | A61C 8/0001 433/27 |
| 2014/0154644 | A1 * | 6/2014 | Kim | A61C 13/01 433/214 |

\* cited by examiner

CENTRIC RELATION BITE REGISTRATION TOOL

BACKGROUND OF THE INVENTION

1. Field of the Invention

The present invention relates to the fabrication of dental prosthetics, and more particularly to a tool for recording a dental patient's centric relation for accurate reproduction of the proper relation for the patient's upper and lower teeth in the dental prosthesis.

2. Description of the Related Art

Due to a wide variety of conditions and situations, a dental patient may lose all of the teeth in his or her maxillary and mandibular arches. In order to replace these missing teeth, a dentist will place implant fixtures in both the maxillary and mandibular arches. In order to fabricate a dental prosthesis for the patient, abutments are attached to those implants, and then crowns are either cemented or screwed to these abutments. In order to properly perform this procedure, it is necessary to record the relation of the mandible to the maxilla.

Generally, in dentistry, the "centric relation" is the mandibular jaw position in which the head of the condyle is situated as far anteriorly and superiorly as it possibly can within the mandibular fossa/glenoid fossa. However, when the patient loses his or her teeth, the centric relation is also lost, thus a way of finding the centric relation is needed in order to achieve the proper relation for the upper and lower teeth to produce good occlusion for the dental prosthesis. In order to find the lost centric relation, it is necessary to use a device that records the exact position of the mandible in relation to the maxilla. Typically, this is performed using an acrylic base material. This acrylic base is fabricated in a laboratory on a cast. Following this, the dentist places this acrylic base over the implant and the mandible is manipulated back to its position. This is followed by using a silicone base registration material. At that that time, the centric relation is recorded back.

The recorded relation may then be sent to the laboratory to begin fabrication of the dental prosthesis in the particular recorded position. This recordation process, however, requires the patient to undergo multiple appointments for the various stages of the procedure, and the process is susceptible to errors and inaccuracies in the centric relation recordation. Thus, a centric relation bite registration tool solving the aforementioned problems is desired.

SUMMARY OF THE INVENTION

The centric relation bite registration tool is a tool for recording the centric relation of a patient's mandible in order to obtain proper occlusion to fabricate a full mouth fixed dental prosthesis. The centric relation bite registration tool includes both a vertically adjustable portion and a horizontally adjustable portion. The vertically adjustable portion is adapted for mounting in a dental implant in the patient's mandibular arch, and the horizontally adjustable portion is adapted for mounting in a dental implant in the patient's maxillary arch. The vertically adjustable portion and the horizontally adjustable portion are releasably secured to one another between the mandibular and maxillary arches providing a single tool which is both horizontally and vertically adjustable for recordation of the proper occlusion between the patient's mandible and maxilla.

The vertically adjustable portion includes a main body portion having opposed first and second ends. A first base portion is mounted on the second end of the main body portion. The first base portion is adapted for removable mounting in the dental implant in the patient's mandibular arch. The vertically adjustable portion also includes a vertically adjustable post which has a free end and a fixed end. The fixed end is housed within the main body portion of the vertically adjustable portion and the free end projects outwardly from the first end of the main body portion. The vertically adjustable post is selectively vertically adjustable with respect to the main body portion and may be selectively locked at a fixed vertical height with respect to the main body portion.

The horizontally adjustable portion includes a frame, which has opposed closed and open ends, and a second base portion which is adapted for removable mounting in the dental implant in the patient's maxillary arch. The second base portion is mounted on the closed end of the frame. A sliding member is received within the frame of the horizontally adjustable portion, such that the sliding member is selectively horizontally adjustable with respect to the frame and may be selectively locked at a fixed horizontal position with respect to the frame. A mount is secured to a central portion of the sliding member. The mount has a recess defined therein for releasably receiving the free end of the vertically adjustable post of the vertically adjustable portion. The free end of the vertically adjustable post engages the mount through the open end of the frame.

In use, the first base of the vertically adjustable portion is attached to the dental implant in the patient's mandibular arch, and the second base of the horizontally adjustable portion is attached to the dental implant in the patient's maxillary arch. The height of the vertically adjustable post is adjusted until it contacts the mount of the horizontally adjustable portion. In this way, the vertical dimension of Me centric relation recordation can be determined. The sliding member is then horizontally adjusted within the frame until the proper horizontal centric relation is determined.

These and other features of the present invention will become readily apparent upon further review of the following specification.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
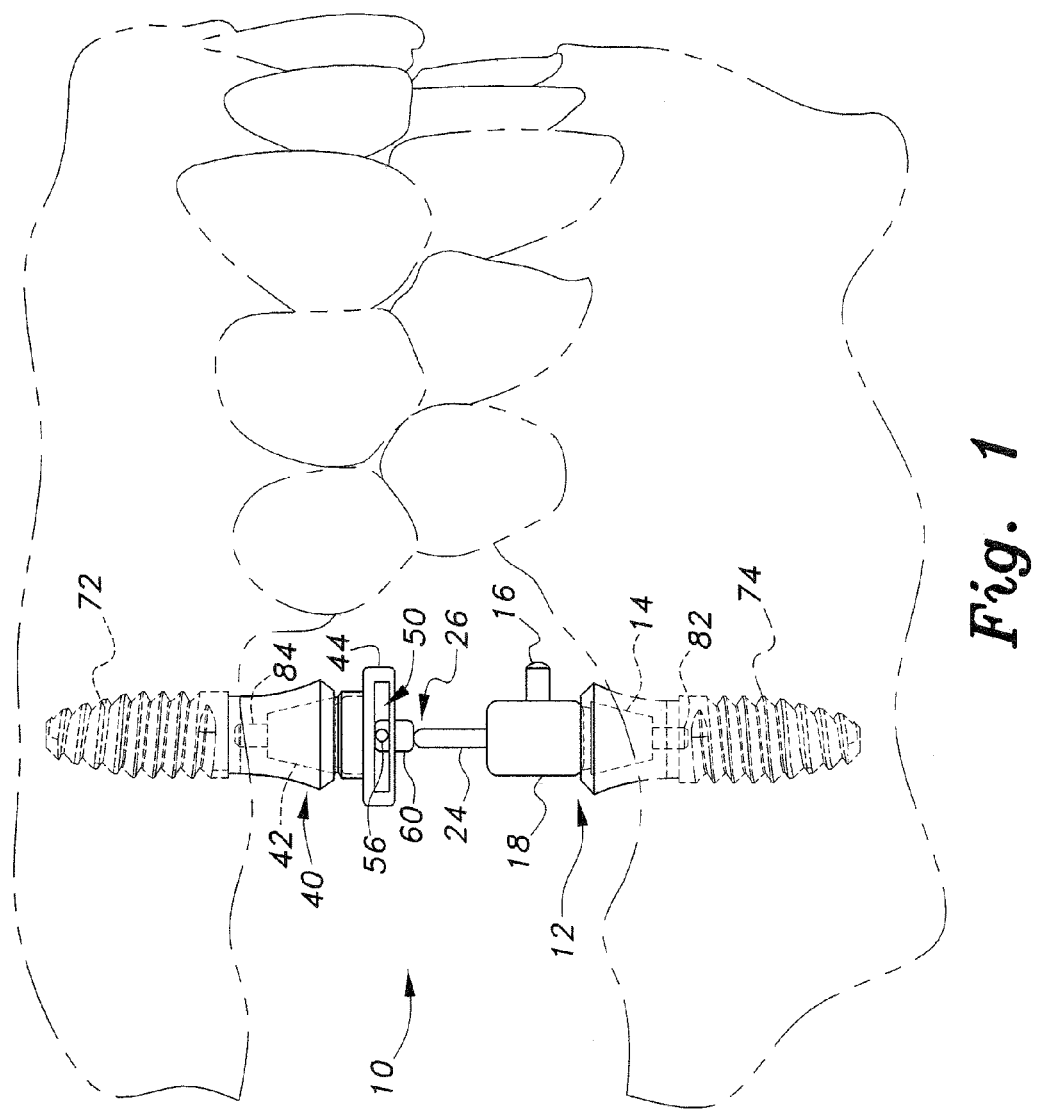
FIG. 1 is an environmental side view of a centric relation bite registration tool according to the present invention.

The centric relation bite registration tool 10 is a tool for recording the centric relation of a patient's mandible in order to obtain proper occlusion to fabricate a full mouth fixed dental prosthesis. As shown in FIG. 1, the centric relation bite registration tool 10 includes both a vertically adjustable portion 12 and a horizontally adjustable portion 40. The vertically adjustable portion 12 is adapted for mounting in a dental implant 74 in the patient's mandibular arch, and the horizontally adjustable portion 40 is adapted for mounting in a dental implant 72 in the patient's maxillary arch. As will be described in greater detail below, the vertically adjustable portion 12 and the horizontally adjustable portion 40 are releasably secured to one another between the mandibular and maxillary arches providing a single tool which is both horizontally and vertically adjustable for recordation of the proper occlusion between the patient's mandible and maxilla.

Figure 2:
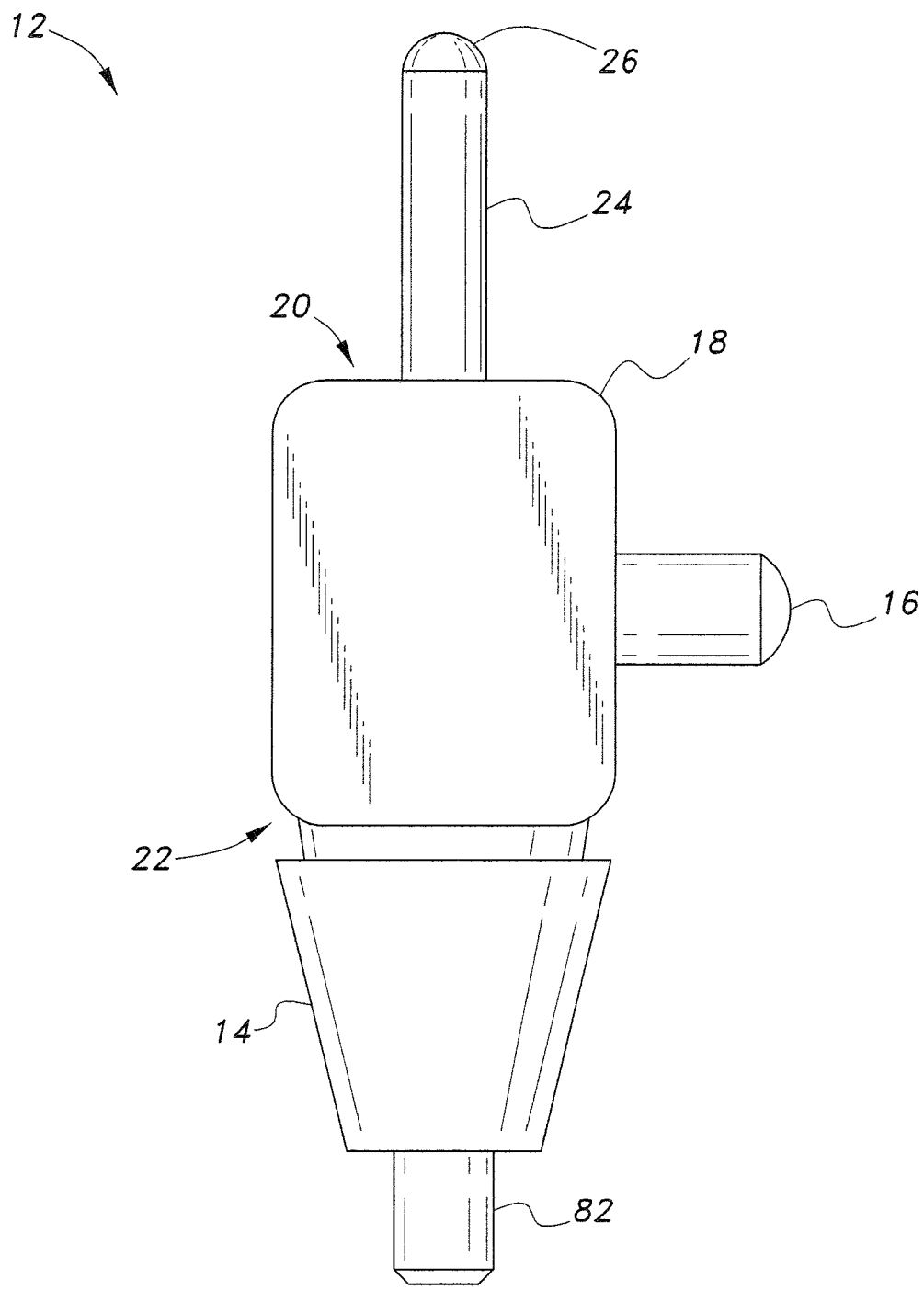
FIG. 2 is a side view of a vertically adjustable portion of the centric relation bite registration tool.
Figure 3:
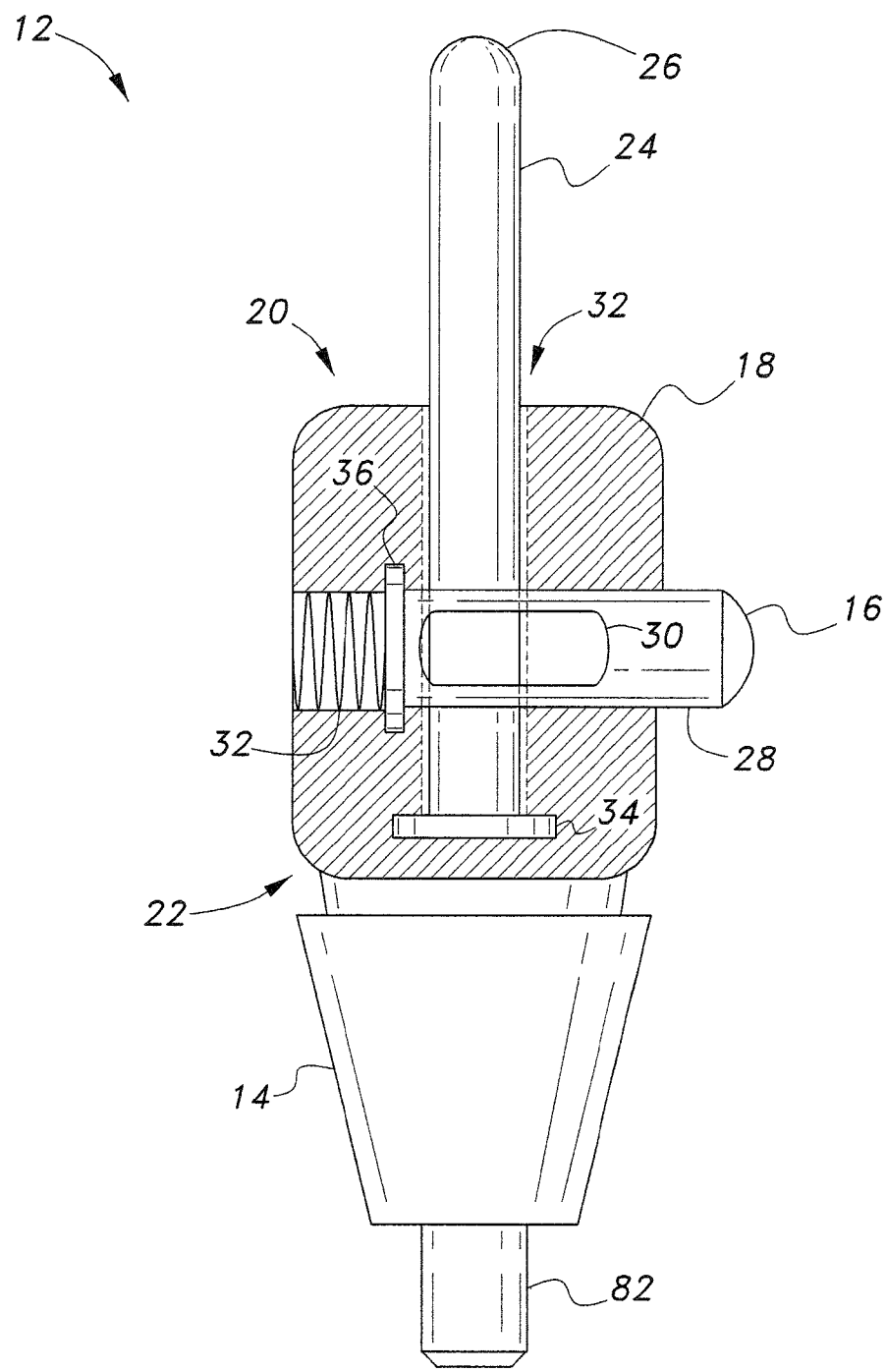
FIG. 3 is a side view in section of the vertically adjustable portion of FIG. 2.
Figure 4:
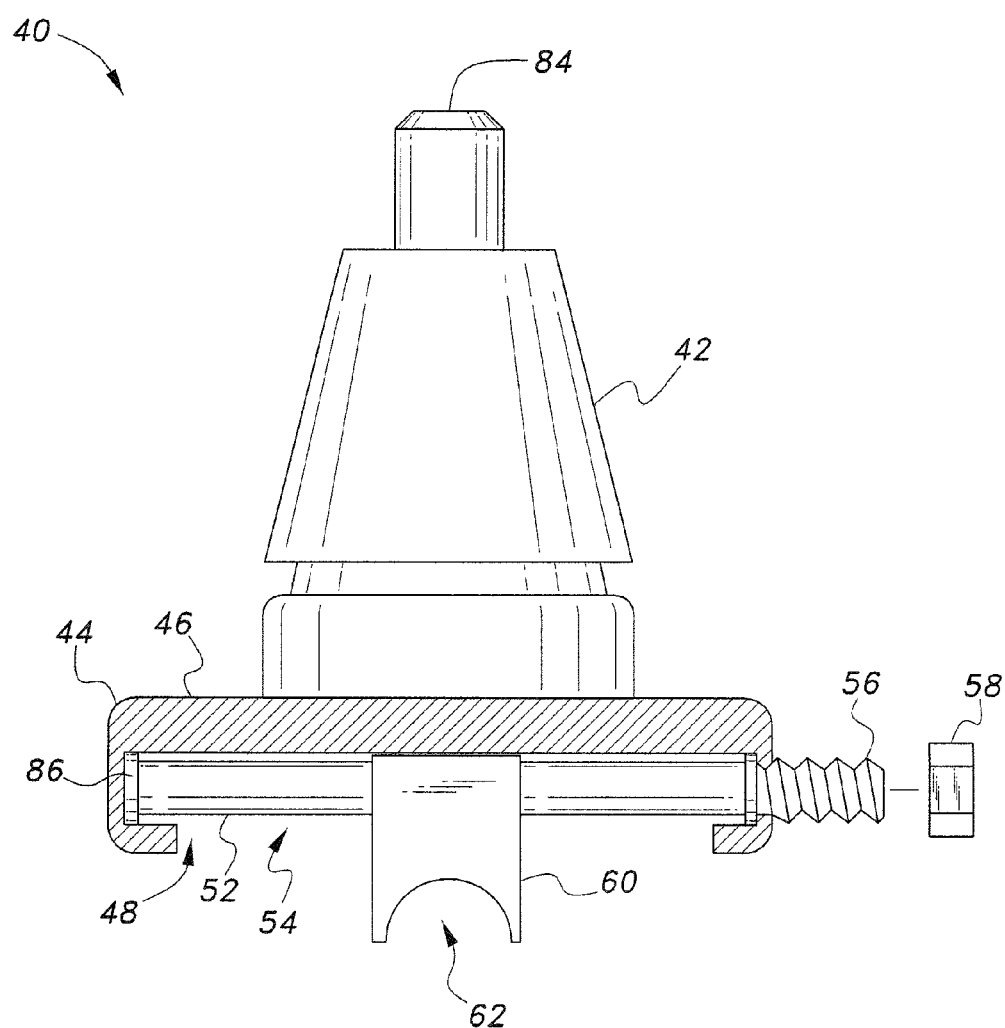
FIG. 4 is a front view of a horizontally adjustable portion of the centric relation bite registration tool in partial section.
Figure 5:
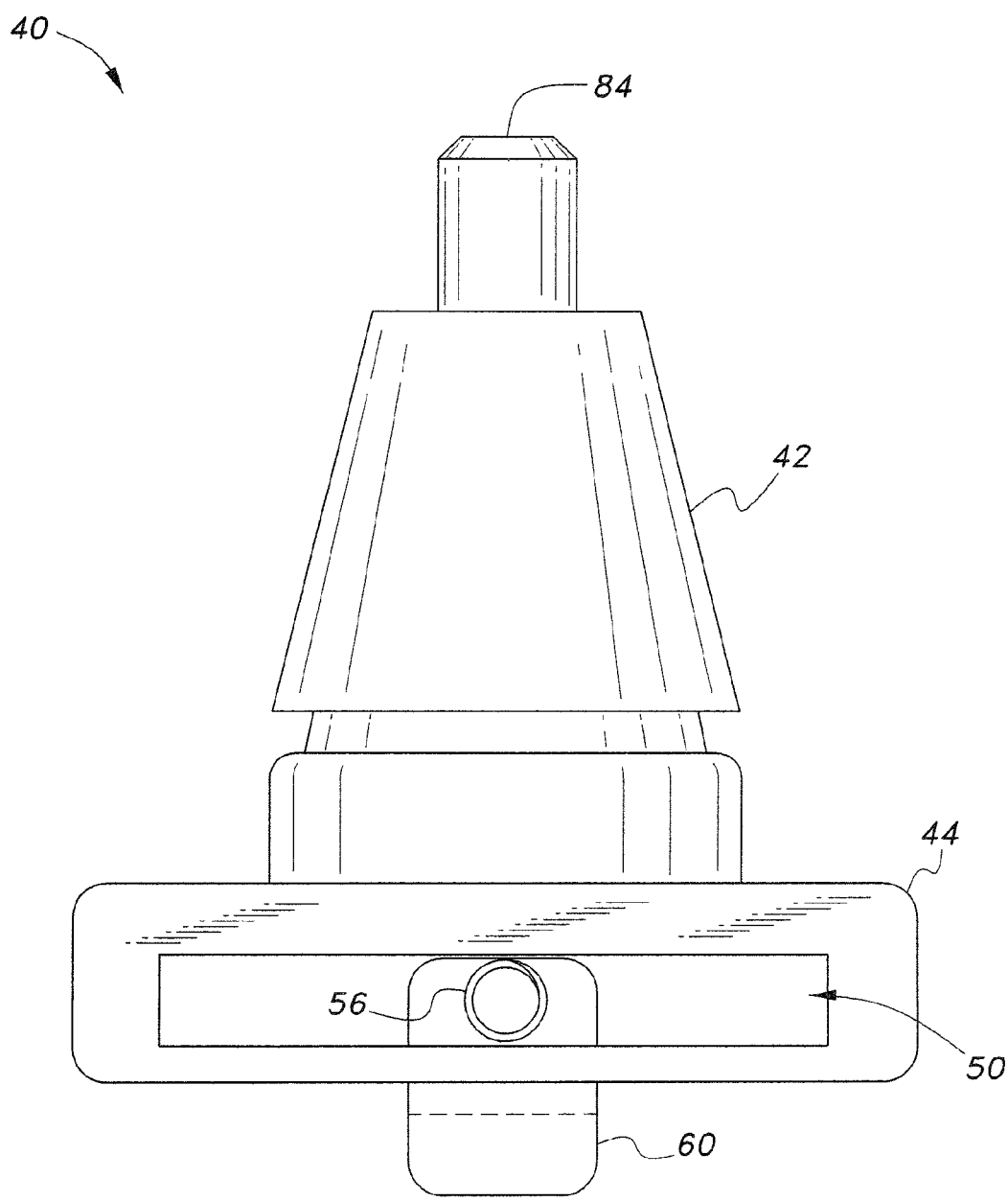
FIG. 5 is a side view of the horizontally adjustable portion FIG. 4.

As best shown in FIGS. 2 and 3, the vertically adjustable portion 12 includes a main body portion 18 having opposed first and second ends 20, 22, respectively. A first base portion 14 is mounted on the second end 22 of main body portion 18. The first base portion 14 is adapted for removable mounting in dental implant 74 in the patient's mandibular arch. Similarly, as shown in FIGS. 4 and 5, the horizontally adjustable portion 40 includes a second base portion 42, which is adapted for removable mounting in dental implant 72 in the patient's maxillary arch. The main body portion 18 is shown as having a substantially cylindrical contour, and each of the first and second base portions 14, 42 are shown as having substantially frustoconical contours with first and second pegs 82, 84 respectively projecting outwardly therefrom. It should be understood that these configurations are exemplary and are shown for use with the particular tissue-level implants 74, 72 shown in the example of FIG. 1. It should be understood that first and second base portions 14, 42 may have any suitable configuration for releasable engagement with any suitable type of dental implants.

The vertically adjustable portion 12 further includes a vertically adjustable post 24. As best shown in FIG. 3, the vertically adjustable post 24 has a free end 26 and a fixed end 34. The fixed end 34, which may include a retaining stop or rim, as shown, is housed within the main body portion 18, and the free end 26 projects outwardly from the first end 20 of main body portion 18.

The vertically adjustable post 24 is selectively vertically adjustable with respect to the main body portion 18 via sliding action through a vertical opening or passage 32. The vertically adjustable post 24 may be selectively locked at a fixed vertical height with respect to the main body portion 18. As best seen in FIG. 3, a push button 28 may be spring-biased (at end or stop 36) via spring or elastic element 32, mounted within main body portion 18. As shown, a substantially oval groove or recess 30 is cut into a central portion of the push button 28 (within main body portion 18) such that positioning of the vertically adjustable post 24 within the center of groove or recess 30 allows for free vertical adjustment thereof, but contact under elastic pressure (via the biasing of spring or elastic element 32) between the vertically adjustable post 24 and the sides of groove or recess 30 provide sufficient frictional force to releasably lock the vertically adjustable post 24 in place. It should, however, be understood that any suitable type of releasable fixture or locking mechanism may be used to releasably lock vertically adjustable post 24 at a desired vertical height with respect to main body portion 18.

As best shown in FIGS. 4 and 5, the horizontally adjustable portion 40 includes a frame 44, which has opposed closed and open ends, 46, 48, respectively, and the second base portion 42 which, as noted above, is adapted for removable mounting in dental implant 72 in the patient's maxillary arch. The second base portion 42 is mounted on the closed end 46 of the frame 44. A sliding member 52 is received within the frame 44, such that the sliding member 52 is selectively horizontally adjustable with respect to frame 44 and may be selectively locked at a fixed horizontal position with respect to the frame 44. As shown, the sliding member 52 has opposed free and fixed ends, 56, 86, respectively, with the fixed end 86 being mounted within frame 44, and with the free end 56 projecting through a horizontally extending slot 50 formed through a sidewall of frame 44. As shown, the free end 56 may be threaded for releasably engaging a nut 68 or the like to hold the sliding member 52 in place with respect to frame 44, although it should be understood that any suitable type of releasable fixture or locking structure may be used to releasably lock the sliding member 52 in a desired horizontal position within the frame 44.

A mount 60 is secured to a central portion 54 of the sliding member 52. The mount 60 has a recess 62 defined therein for releasably receiving the free end 26 of the vertically adjustable post 24 of the vertically adjustable portion 12. The free end 26 of the vertically adjustable post 24 engages the mount 60 through the open end 48 of the frame 44. Mount 60 may be adjustable along the axial direction of sliding member 52, allowing the positioning of mount 60 to be horizontally adjustable along two axes.

In use, the base 14 of vertically adjustable portion 12 is attached to implant 74 in the patient's mandibular arch, and base 42 of horizontally adjustable portion 40 is attached to implant 72 in the patient's maxillary arch, as shown in FIG. 1. The height of vertically adjustable post 24 is adjusted until it contacts the mount 60 (with free end 26 engaging recess 62) of the horizontally adjustable portion 40. In this way, the vertical dimension of the centric relation recordation can be determined. The sliding member 52 is then horizontally adjusted within frame 44 until the proper horizontal centric relation is determined.

The centric relation bite registration tool 10 can be made from a reusable material, such as a sterilizeable plastic.

It is to be understood that the present invention is not limited to the embodiments described above, but encompasses any and all embodiments within the scope of the following claims.

We claim:
1. A centric relation bite registration tool, comprising:
   a vertically adjustable portion; including:
      a main body portion having opposed first and second ends, the main body portion further including vertical and horizontal passages therethrough;
      a first base portion, a first engaging peg projecting outwardly from the first base portion and adapted for removable mounting in a dental implant in a patient's mandibular arch, the first base portion being mounted on the second end of the main body portion;
      a vertically adjustable post, the vertically adjustable post being selectively vertically adjustable with respect to the main body portion via sliding action through the vertical passage, the vertically adjustable post having a free end and a fixed end, the fixed end thereof being housed within the main body portion of said vertically adjustable portion, the free end thereof projecting outwardly from the first end of the main body portion;
      a spring-biased button mounted in the horizontal passage in the main body portion, the spring-biased button having a recess configured and dimensioned to receive the vertically adjustable post therein, the spring-biased button defining a release for securing the vertically adjustable post at a fixed vertical height with respect to the main body portion of said vertically adjustable portion; and a horizontally adjustable portion, including:

a frame having opposed closed and open ends;

a second base portion, a second engaging peg projecting outwardly from the second base portion and adapted for removable mounting in a dental implant in the patient's maxillary arch, the second base portion being mounted on the closed end of the frame;

a sliding member received within the frame of said horizontally adjustable portion, wherein the sliding member is selectively horizontally adjustable with respect to the frame, further wherein the sliding member of said horizontally adjustable portion has opposed free and fixed ends, the fixed end thereof being mounted within the frame, the free end thereof projecting through a horizontally extending slot formed through the frame;

means for releasably securing the sliding member in a fixed horizontal position with respect to the frame;

a mount secured to a central portion of the sliding member, the mount having a recess defined therein for releasably receiving the free end of the vertically adjustable post of the vertically adjustable portion, wherein the free end of the vertically adjustable post engages the mount through the open end of the frame.

2. The centric relation bite registration tool as recited in claim 1, wherein the main body portion of said vertically adjustable portion has a substantially cylindrical contour.

3. The centric relation bite registration tool as recited in claim 2, wherein the first base portion of said vertically adjustable portion has a substantially frustoconical contour.

4. The centric relation bite registration tool as recited in claim 1, wherein the second base portion of said horizontally adjustable portion has a substantially frustoconical contour.

5. The centric relation bite registration tool as recited in claim 1, wherein the free end of the sliding member is threaded for releasably engaging a nut.

* * * * *